(12) United States Patent
Jung et al.

(10) Patent No.: US 12,350,026 B2
(45) Date of Patent: Jul. 8, 2025

(54) PHOTOPLETHYSMOGRAPHY SENSOR AND SEMICONDUCTOR DEVICE INCLUDING THE SAME

(71) Applicant: Samsung Electronics Co., Ltd., Suwon-si (KR)

(72) Inventors: Sung Jin Jung, Hwaseong-si (KR); Long Yan, Hwaseong-si (KR); Seoung Jae Yoo, Seongnam-si (KR); Yun-Cheol Han, Yongin-si (KR)

(73) Assignee: Samsung Electronics Co., Ltd., Gyeonggi-do (KR)

( * ) Notice: Subject to any disclaimer, the term of this patent is extended or adjusted under 35 U.S.C. 154(b) by 823 days.

(21) Appl. No.: 17/192,418

(22) Filed: Mar. 4, 2021

(65) Prior Publication Data

US 2022/0007953 A1    Jan. 13, 2022

(30) Foreign Application Priority Data

Jul. 10, 2020 (KR) .......................... 10-2020-0085492

(51) Int. Cl.
*A61B 5/024* (2006.01)
*A61B 5/00* (2006.01)

(52) U.S. Cl.
CPC ........ *A61B 5/02427* (2013.01); *A61B 5/0004* (2013.01); *A61B 5/02438* (2013.01); *A61B 5/681* (2013.01)

(58) Field of Classification Search
CPC ............. A61B 5/02427; A61B 5/0004; A61B 5/02438; A61B 5/681
See application file for complete search history.

(56) References Cited

U.S. PATENT DOCUMENTS

| 6,912,413 | B2 | 6/2005 | Rantala et al. |
| 8,530,819 | B2 | 9/2013 | Ritter et al. |
| (Continued) |

FOREIGN PATENT DOCUMENTS

| CN | 105491943 A | 4/2016 |
| CN | 107920787 A | 4/2018 |
| (Continued) |

OTHER PUBLICATIONS

Chinese Office Action dated Mar. 13, 2025 issued in corresponding Chinese Patent Appln. No. 202110760454.9.

*Primary Examiner* — Allen Porter
*Assistant Examiner* — Megan T Fedorky
(74) *Attorney, Agent, or Firm* — Harness, Dickey & Pierce, P.L.C.

(57) ABSTRACT

A photoplethysmography sensor that includes a photoelectric conversion element including a first terminal and a second terminal, and that receives light reflected from a blood vessel and generates a current corresponding to the received light, a current-to-voltage converter that receives the generated current through a first input terminal and a second input terminal, and generates an output voltage corresponding to the received current, and a switch that, in response to a control signal of a first level, connects the first and second terminals of the photoelectric conversion element respectively to the first and second input terminals of the current-to-voltage converter and in response to the control signal of a second level different from the first level, connects the first and second terminals of the photoelectric conversion element respectively to the second and first input terminals of the current-to-voltage converter.

19 Claims, 13 Drawing Sheets

(56) References Cited

U.S. PATENT DOCUMENTS

| | | | |
|---|---|---|---|
| 9,215,114 B2 * | 12/2015 | Emami-Neyestanak | ................... H03F 1/08 |
| 9,742,420 B2 | 8/2017 | Narayanan et al. | |
| 10,568,530 B2 | 2/2020 | Finlinson et al. | |
| 2014/0243622 A1 * | 8/2014 | Crowe | ................ A61B 5/7228 600/479 |
| 2016/0235313 A1 * | 8/2016 | Sharma | ................ A61B 5/7228 |
| 2016/0374574 A1 | 12/2016 | Finlinson et al. | |
| 2017/0042435 A1 * | 2/2017 | Vermeulen | ......... A61B 5/02416 |
| 2017/0238826 A1 | 8/2017 | Finlinson | |
| 2019/0082985 A1 | 3/2019 | Hong et al. | |

FOREIGN PATENT DOCUMENTS

| | | | |
|---|---|---|---|
| CN | 110338776 A1 * | 10/2019 | ............... H03F 3/08 |
| JP | 6455994 B2 * | 1/2019 | ......... A61B 5/02416 |
| WO | WO-2013/190423 A1 | 12/2013 | |
| WO | WO-2017113758 A1 * | 7/2017 | ......... A61B 5/02427 |

* cited by examiner

PHOTOPLETHYSMOGRAPHY SENSOR AND SEMICONDUCTOR DEVICE INCLUDING THE SAME

CROSS-REFERENCE TO RELATED APPLICATION

This application claims priority from Korean Patent Application No. 10-2020-0085492 filed on Jul. 10, 2020 in the Korean Intellectual Property Office, and all the benefits accruing therefrom under 35 U.S.C. 119, the contents of which in its entirety are herein incorporated by reference.

BACKGROUND

1. Technical Field

The present disclosure relates to a photoplethysmography (PPG) sensor and a semiconductor device including the PPG sensor.

2. Description of the Related Art

A pulse wave sensor is a sensor that measures a photoplethysmography signal (hereinafter, referred to as a PPG signal or a pulse wave signal) from a subject by using a light pulse.

When sensing the pulse wave signal, noise such as external light interference, sound, vibration, or motion may be simultaneously inputted to a sensor input unit, together with the pulse wave signal. At this time, if the noise component is very large compared to the pulse wave signal, the measurement sensitivity may deteriorate. Therefore, there is a need for research on a method for more efficiently removing such noise.

SUMMARY

Aspects of the present disclosure provide a photoplethysmography sensor capable of efficiently removing noise when measuring a pulse wave signal.

Aspects of the present disclosure also provide a semiconductor device capable of efficiently removing noise when measuring a pulse wave signal.

According to some aspects of the present inventive concepts, there is provided a photoplethysmography sensor comprises a photoelectric conversion element including a first terminal and a second terminal, and configured to receive light reflected from a blood vessel and generate a current corresponding to the received light, a current-to-voltage converter configured to receive the generated current through a first input terminal and a second input terminal, and configured to generate an output voltage corresponding to the received current, and a switch configured to connect the photoelectric conversion element to the current-to-voltage converter according to a control signal, wherein in response to the control signal of a first level, the switch connects the first terminal of the photoelectric conversion element to the first input terminal of the current-to-voltage converter, and connects the second terminal of the photoelectric conversion element to the second input terminal of the current-to-voltage converter, and wherein in response to the control signal of a second level different from the first level, the switch connects the first terminal of the photoelectric conversion element to the second input terminal of the current-to-voltage converter, and connects the second terminal of the photoelectric conversion element to the first input terminal of the current-to-voltage converter.

According to some aspects of the present inventive concepts, there is provided a semiconductor device comprises a light source configured to output light during a first time section, and configured not to output the light during a second time section following the first time section, and a detector configured to receive light outputted from the light source and reflected from a blood vessel, and configured to generate a first output voltage corresponding to light received during the first and second time sections, wherein the detector includes a photoelectric conversion element configured to generate electric charges corresponding to the received light, and a storage unit configured to store the generated electric charges and generate the output voltage, and wherein an amount of electric charges in the storage unit increases corresponding to electric charges generated by the photoelectric conversion element during the first time section, and decreases corresponding to electric charges generated by the photoelectric conversion element during the second time section.

According to some aspects of the present inventive concepts, there is provided a semiconductor device comprises a light source configured to output light according to a first control signal having a first period, and modulate and output the light according to a second control signal having a second period shorter than the first period, a photoelectric conversion element configured to receive light outputted from the light source and reflected from a blood vessel, and generate a current corresponding to the received light, a current-to-voltage converter configured to generate an output voltage corresponding to the current generated from the photoelectric conversion element, and a switch configured to perform a first connection between the photoelectric conversion element and the current-to-voltage converter in response to the second control signal of a first level, and perform a second connection different from the first connection between the photoelectric conversion element and the current-to-voltage converter in response to the second control signal of a second level different from the first level.

However, aspects of the present disclosure are not restricted to those set forth herein. The above and other aspects of the present disclosure will become more apparent to one of ordinary skill in the art to which the present disclosure pertains by referencing the detailed description of the present disclosure given below.

BRIEF DESCRIPTION OF THE DRAWINGS

The above and other aspects and features of the present disclosure will become more apparent by describing in detail example embodiments thereof with reference to the attached drawings, in which.

DETAILED DESCRIPTION OF EXAMPLE EMBODIMENTS

Hereinafter, example embodiments of the present disclosure will be described with reference to the accompanying drawings.

Figure 1:
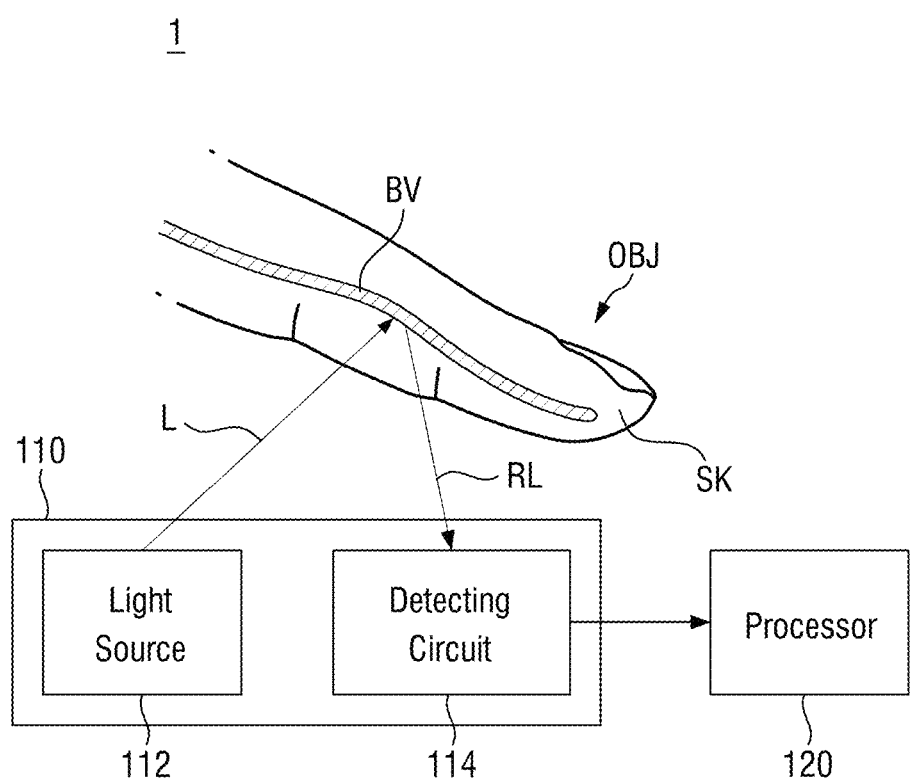
FIG. 1 is a block diagram of a semiconductor device according to some example embodiments.
Figure 2:
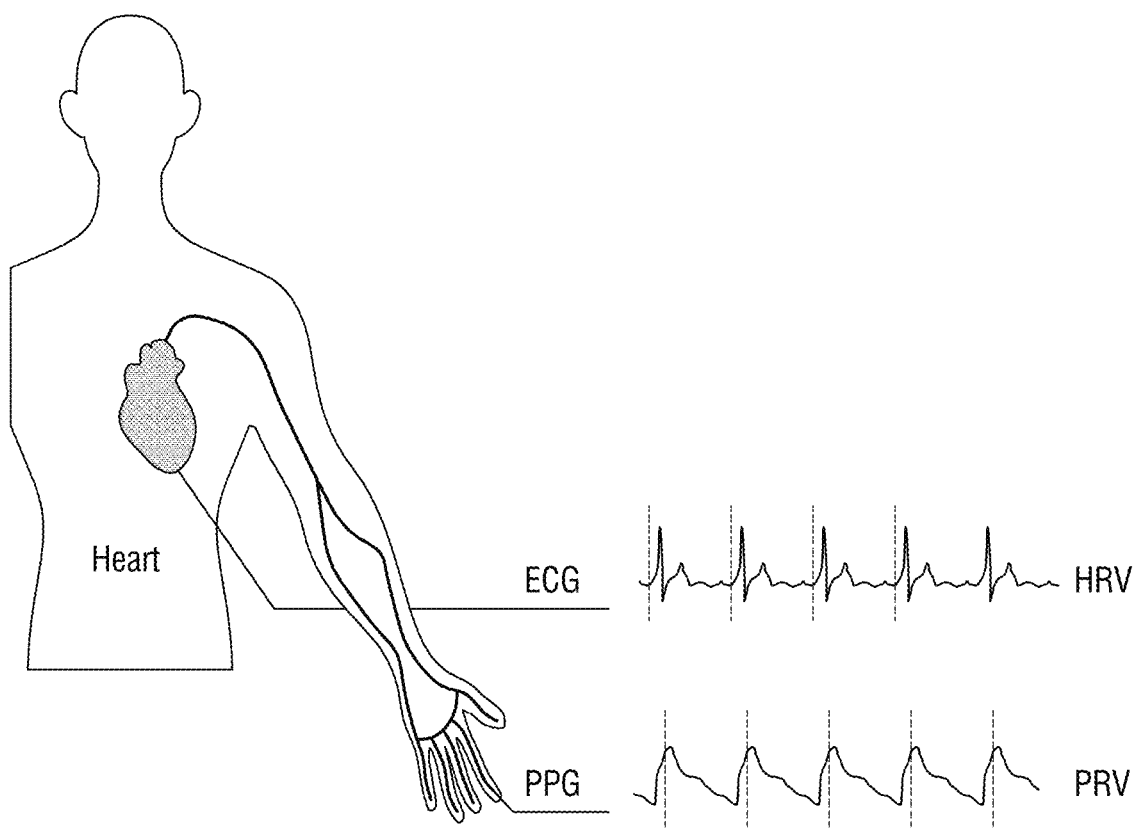
FIG. 2 is a diagram illustrating an application example of a processor according to some example embodiments.

FIG. 1 is a block diagram of a semiconductor device according to some example embodiments. FIG. 2 is a diagram illustrating an application example of a processor according to some example embodiments.

Referring to FIG. 1, a semiconductor device 1 may include a pulse wave sensor 110 (or PPG sensor) and a processor 120.

In some example embodiments, the semiconductor device 1 may be, for example, a pulse wave measuring device. The semiconductor device 1 may be mounted on an electronic device such as a smartphone, a tablet PC, a desktop PC, or a laptop PC, or on a medical device of a specialized medical institution. Alternatively, the semiconductor device 1 may be manufactured in an independent form such as a wearable device, which is wearable on a subject, such as a wrist watch type, a bracelet type, a wrist band type, a ring type, a glasses type, or a hair band type.

The pulse wave sensor 110 may sense a pulse wave signal (or PPG signal) from a subject OBJ by using a light pulse outputted from a light source 112. The pulse wave sensor 110 may include the light source 112 that irradiates light L to the subject OBJ, and a detector 114 that detects, when the light L irradiated by the light source 112 is reflected from biological tissue such as the surface of skin SK or a blood vessel BV, reflected light RL.

The PPG signal is a waveform that reflects a change in volume of blood vessels depending on the heartbeat in the peripheral region. When a heart contracts, blood ejected from a left ventricle of the heart moves to peripheral tissues, which increases the arterial blood volume. Further, when the heart contracts, red blood cells carry more oxygen hemoglobin to the peripheral tissues. When the heart relaxes, the heart receives a partial influx of blood from the peripheral tissues. When light L is irradiated to peripheral blood vessels, the irradiated light L is absorbed by the peripheral tissues. Light absorbance depends on hematocrit and blood volume. The light absorbance may have a maximum value when the heart contracts and may have a minimum value when the heart relaxes.

The pulse wave signal reflects the maximum value of the light absorbance when the heart contracts and reflects the minimum value of the light absorbance when the heart relaxes. In addition, the pulse wave signal vibrates according to the heartbeat cycle. Therefore, since the pulse wave signal reflects a change in blood pressure depending on the heartbeat, it may be used, for example, for blood pressure measurement.

The light source 112 may irradiate light of one or more different wavelengths. For example, the different wavelengths may include blue, green, red, and infrared wavelengths, but example embodiments are not limited thereto.

The light source 112 may be composed of, for example, a light emitting diode (LED), a laser diode (LD), a phosphor, or the like, but is not limited thereto.

In some example embodiments, the light source 112 includes a plurality of light sources, and the plurality of light sources may be arranged at different distances from the detector 114.

The detector 114 may include one or more pixels that detect the reflected light RL reflected from the biological tissue of the subject OBJ and convert it into an electrical signal. The one or more pixels may include a photodiode, a photo transistor (PTr), an image sensor (e.g., CMOS image sensor), or the like, but example embodiments are not limited thereto.

The processor 120 may receive the pulse wave signal from the pulse wave sensor 110 and perform various signal processing using the received pulse wave signal. For example, the processor 120 may extract various features for estimating blood sugar from the received pulse wave signal. Further, for example, as shown in FIG. 2, the processor 120 may extract pulse rate variability (PRV), heart rate variability (HRV), heart rate, pulse rate, blood vessel stiffness, blood pressure, perfusion index, pulsatile volume, and the like from the received pulse wave signal.

In the drawing, the pulse wave sensor 110 and the processor 120 are illustrated as being separately configured, but example embodiments are not limited thereto, and according to example embodiments, the processor 120 may be implemented to be integrated in the pulse wave sensor 110.

Hereinafter, a more detailed configuration of a pulse wave sensor according to some example embodiments will be described with reference to FIG. 3.

Figure 3:
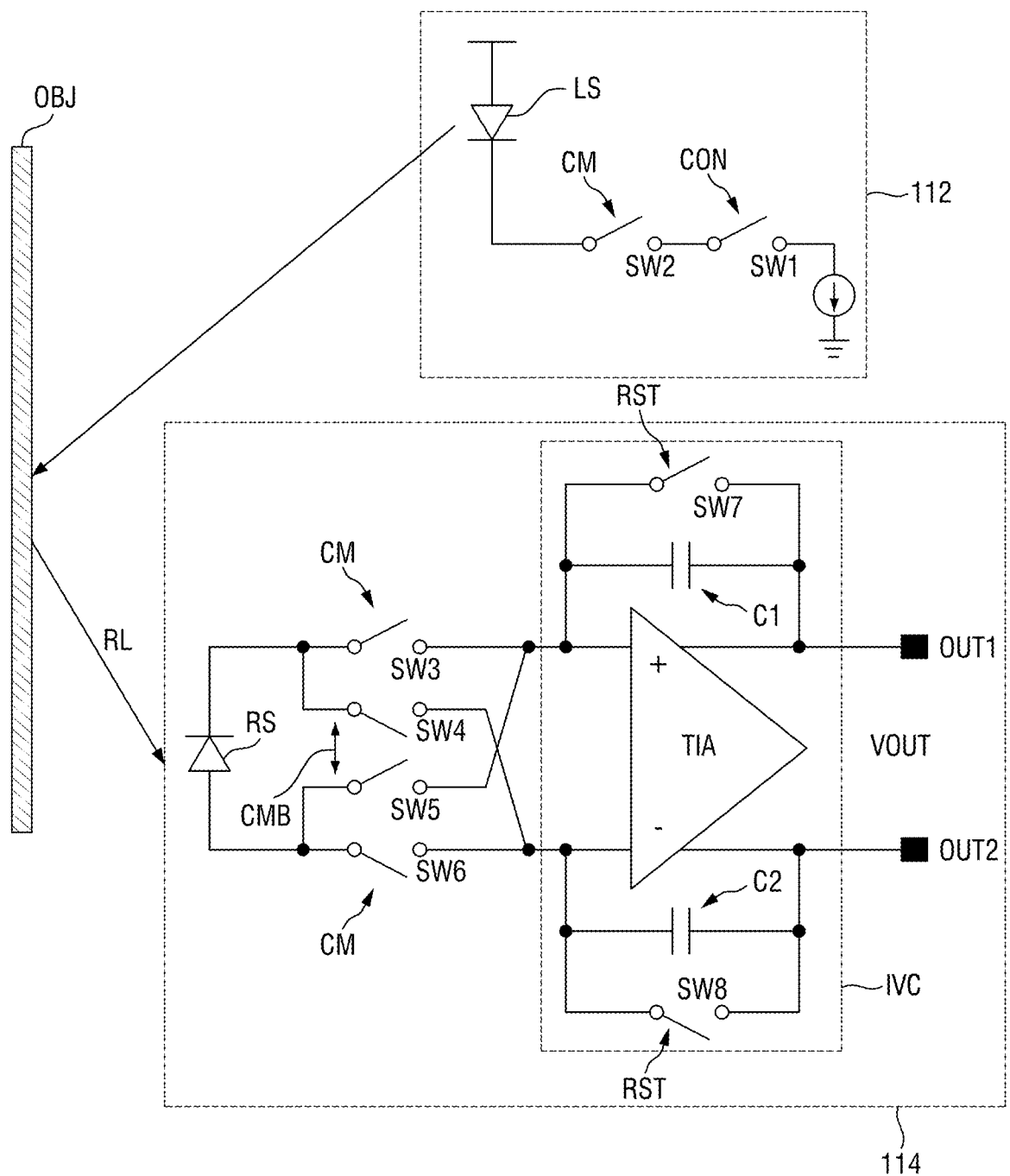
FIG. 3 is a circuit diagram of the pulse wave sensor of FIG. 1.

FIG. 3 is a circuit diagram of the pulse wave sensor of FIG. 1.

Referring to FIG. 3, the light source 112 may include a light emitting element LS and switches SW1 and SW2.

The light emitting element LS may generate light L proportional to an applied current or voltage. Although the drawing shows a light emitting diode as an example of the light emitting element LS, example embodiments are not limited thereto.

The switch SW1 may be turned on/off by a control signal CON. The switch SW2 may be turned on/off by a control signal CM.

For example, in response to the control signal CON of a first level (e.g., a logic high level (hereinafter, H-level)), the switch SW1 may be turned on to connect the light emitting element LS to a current source. In addition, in response to the control signal CON of a second level (e.g., a logic low level (hereinafter, L-level)), the switch SW1 may be turned off to disconnect the light emitting element LS from the current source.

In response to the control signal CM of the H-level, the switch SW2 may be turned on to connect the light emitting element LS to the current source. In response to the control signal CM of the L-level, the switch SW2 may be turned off to disconnect the light emitting element LS from the current source.

Here, the control signal CON may be an emission control signal of the light emitting element LS, and the control signal CM may be a modulation control signal.

That is, while the control signal CON maintains the H-level, the control signal CM may repeatedly transition between the H-level and the L-level to allow the light L outputted from the light source 112 to become a light pulse having a certain period. That is, the switch SW2 may serve as a kind of modulator.

On the other hand, while the control signal CON maintains the L-level, the light L is not outputted from the light source 112 regardless of the level of the control signal CM.

In the drawing, the switch SW1 controlled by the control signal CON, which is the emission control signal, and the switch SW2 controlled by the control signal CM, which is the modulation control signal, are separately illustrated, but example embodiments are not limited thereto. The light source 112 may also be configured with only one switch by using a control signal obtained by an AND operation of the control signal CON and the control signal CM.

Further, in some other example embodiments, the light source 112 may also be configured without the illustrated switches. For example, when a control current and a control voltage for controlling the light emitting element LS are applied as a waveform obtained by the AND operation of the control signal CON and the control signal CM, the light source 112 may be configured without a switch. In addition, even when a logic similar to the above is implemented in software that controls the light emitting element LS, the light source 112 may be configured without a switch.

The detector 114 may include a photoelectric conversion element RS, switches SW3, SW4, SW5, and SW6, and/or a current-to-voltage converter IVC.

The photoelectric conversion element RS may generate electric charges (or current) corresponding to received light. Although a photodiode is illustrated as an example in the drawing, example embodiments are not limited thereto. When the photoelectric conversion element RS is the photodiode, the photoelectric conversion element RS may include an anode terminal and a cathode terminal.

In the light received by the photoelectric conversion element RS, not only the reflected light RL irradiated from the light source 112 and reflected from the subject OBJ, but also light (e.g., noise) provided from an external environment exists. Accordingly, it is advantageous to remove such noise from the light received by the photoelectric conversion element RS to obtain an accurate pulse wave signal (or PPG signal) from the reflected light RL.

The current-to-voltage converter IVC may generate an output voltage VOUT corresponding to the electric charges (or current) generated from the photoelectric conversion element RS. The output voltage VOUT may be outputted through, for example, an output terminal OUT1 and an output terminal OUT2.

The current-to-voltage converter IVC may include a transimpedance amplifier (hereinafter, TIA), storage elements C1 and C2, and/or switches SW7 and SW8.

The TIA may include, for example, a first input terminal (+) and a second input terminal (−). The storage element C1 may be connected between the first input terminal (+) and the output terminal OUT1. The storage element C2 may be connected between the second input terminal (−) and the output terminal OUT2.

The switch SW7 may be connected between the first input terminal (+) and the output terminal OUT1. The switch SW8 may be connected between the second input terminal (−) and the output terminal OUT2. The switches SW7 and SW8 may be controlled to be turned on/off by a reset control signal RST.

The switch SW7 may be turned on, for example, by the H-level reset control signal RST to reset the storage element C1. For example, electric charges in the storage element C1 may be removed. The switch SW8 may be turned on, for example, by the H-level reset control signal RST to reset the storage element C2. For example, electric charges in the storage element C2 may be removed.

In some example embodiments, the charge capacity of the storage element C1 and the charge capacity of the storage element C2 may be the same. However, example embodiments are not limited thereto, and if necessary, the charge capacities of the storage elements C1 and C2 may be variously modified and implemented.

The switches SW3, SW4, SW5, and SW6 may switch a connection relationship between the photoelectric conversion element RS and the current-to-voltage converter IVC. For example, the switches SW3, SW4, SW5, and SW6 may be turned on/off by the control signal CM to switch the connection relationship between the photoelectric conversion element RS and the current-to-voltage converter IVC.

For example, the switches SW3 and SW6 may be turned on/off by the control signal CM, and the switches SW4 and SW5 may be turned on/off by a control signal CMB obtained by inverting the control signal CM. Therefore, when the switches SW3 and SW6 are turned on, the switches SW4 and SW5 are turned off, and when the switches SW3 and SW6 are turned off, the switches SW4 and SW5 are turned on.

When the switches SW3 and SW6 are turned on and the switches SW4 and SW5 are turned off, the cathode terminal of the photoelectric conversion element RS is connected to the first input terminal (+) of the current-to-voltage converter IVC, and the anode terminal of the photoelectric conversion element RS is connected to the second input terminal (−) of the current-to-voltage converter IVC. Accordingly, the current generated from the photoelectric conversion element RS charges the storage elements C1 and C2 with electric charges. That is, the amount of electric charges in the storage elements C1 and C2 increases. Accordingly, the output voltage VOUT increases.

Conversely, when the switches SW3 and SW6 are turned off and the switches SW4 and SW5 are turned on, the cathode terminal of the photoelectric conversion element RS is connected to the second input terminal (−) of the current-to-voltage converter IVC, and the anode terminal of the photoelectric conversion element RS is connected to the first input terminal (+) of the current-to-voltage converter IVC. Accordingly, the current generated from the photoelectric conversion element RS discharges the electric charges stored in the storage elements C1 and C2. That is, the amount of electric charges in the storage elements C1 and C2 decreases. Accordingly, the output voltage VOUT decreases. This will be described in more detail later.

Although the drawing shows an example in which the connection relationship between the photoelectric conversion element RS and the current-to-voltage converter IVC is switched using the four switches SW3, SW4, SW5, and SW6, example embodiments are not limited thereto. If necessary, it is also possible to switch the connection relationship between the photoelectric conversion element RS and the current-to-voltage converter IVC by using other methods.

Hereinafter, an operation of the pulse wave sensor will be described in a time domain with reference to FIGS. 3 to 8.

Figure 4:
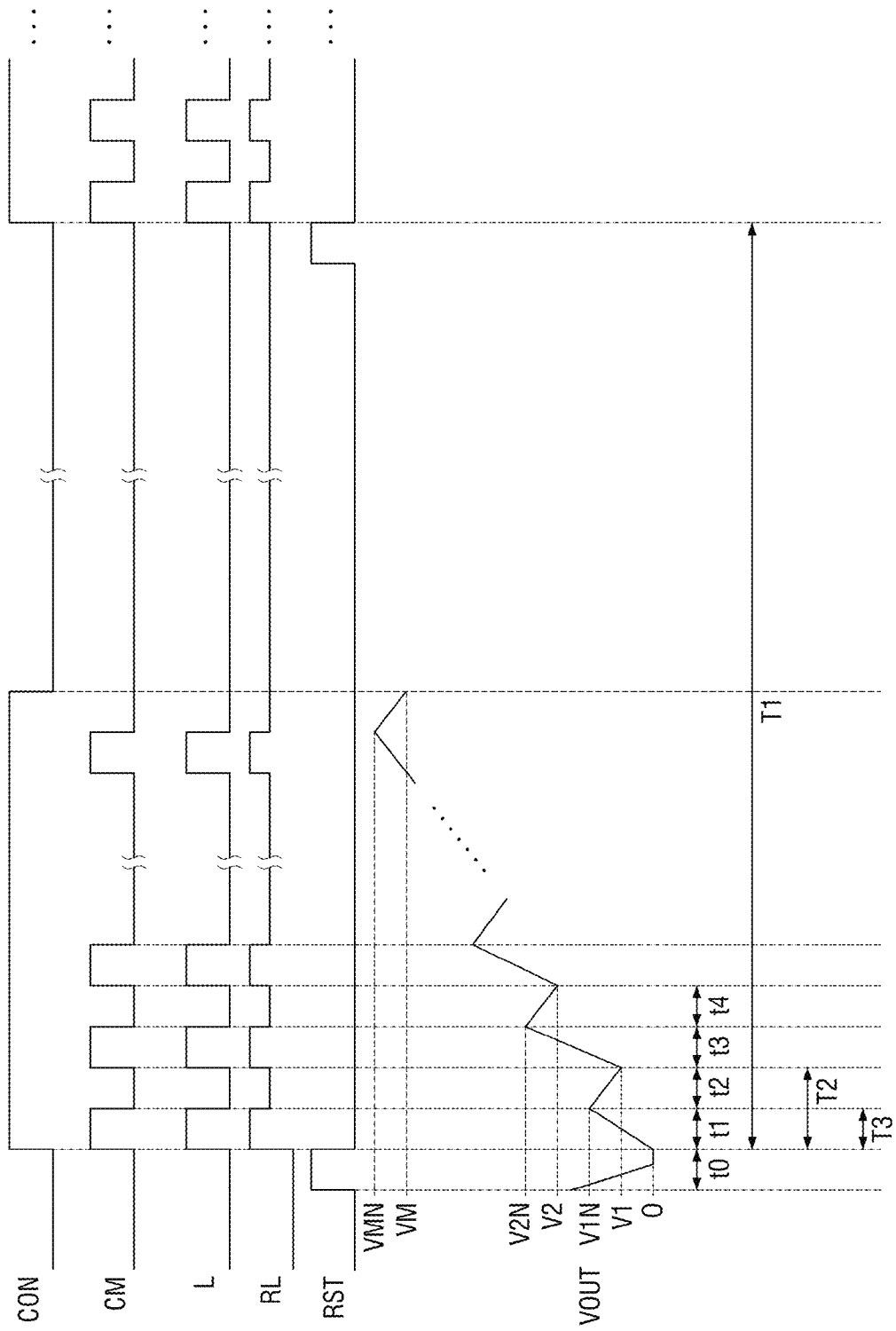
FIGS. 4 and 5 are timing diagrams describing an operation of a pulse wave sensor according to some example embodiments.
Figure 5:
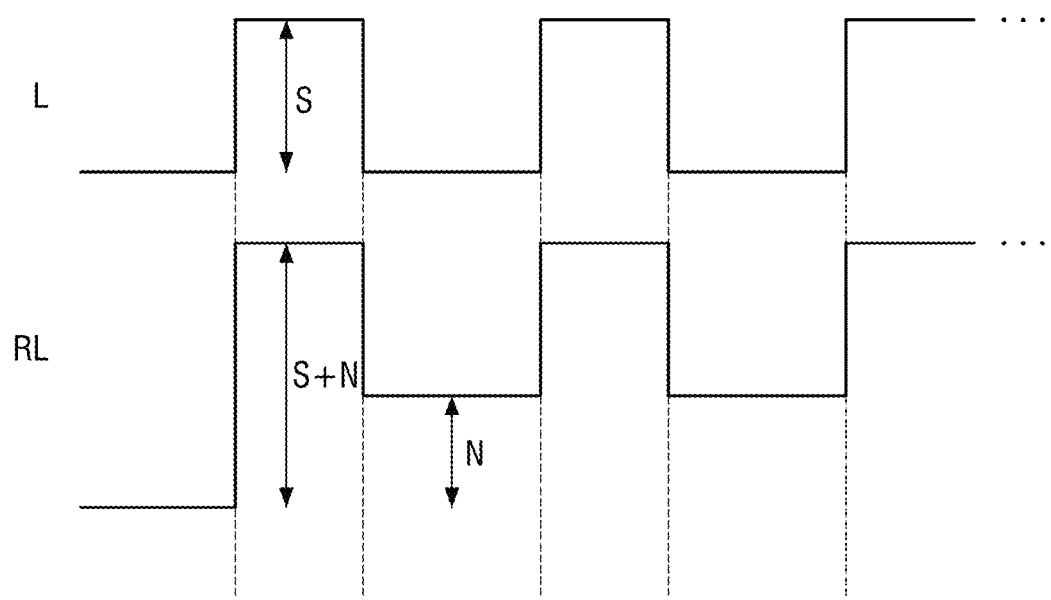
Figure 6:
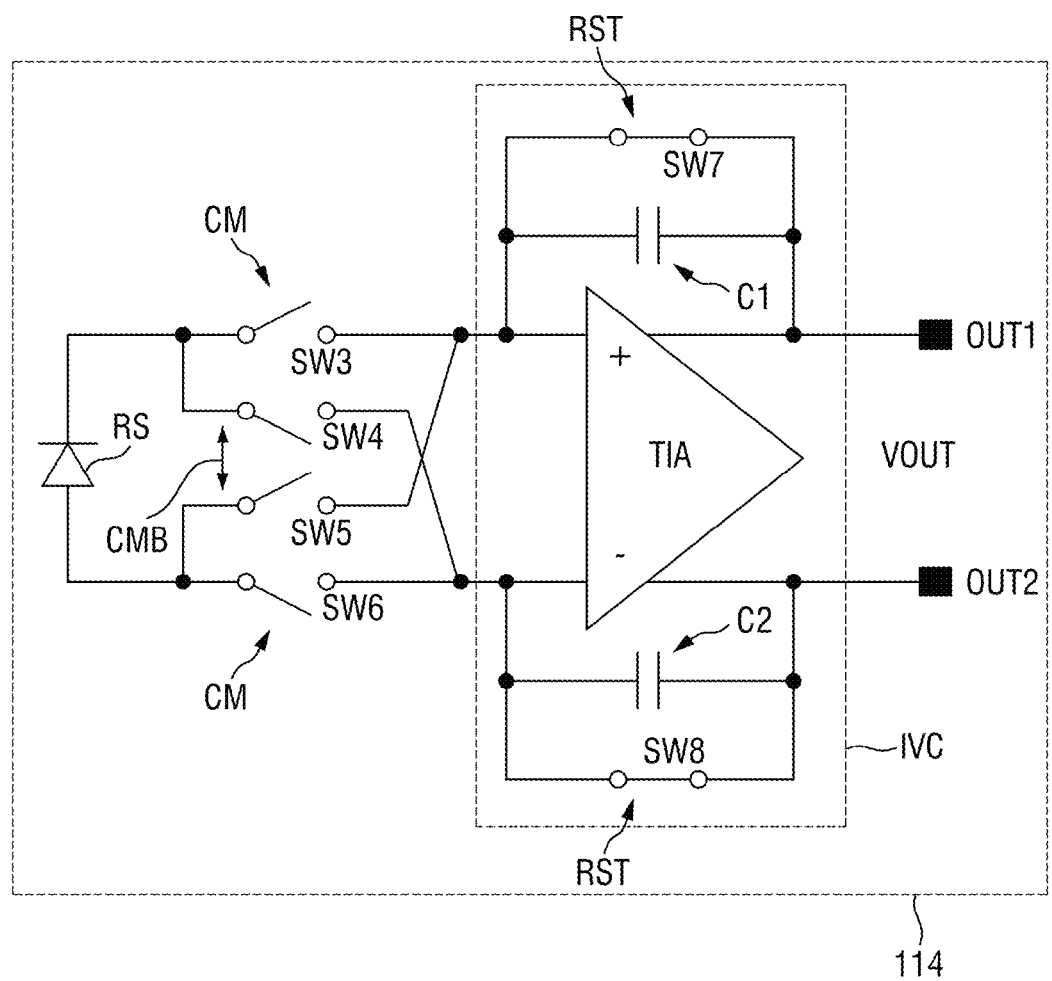
FIGS. 6 to 8 are diagrams describing an operation of a pulse wave sensor according to some example embodiments.
Figure 7:
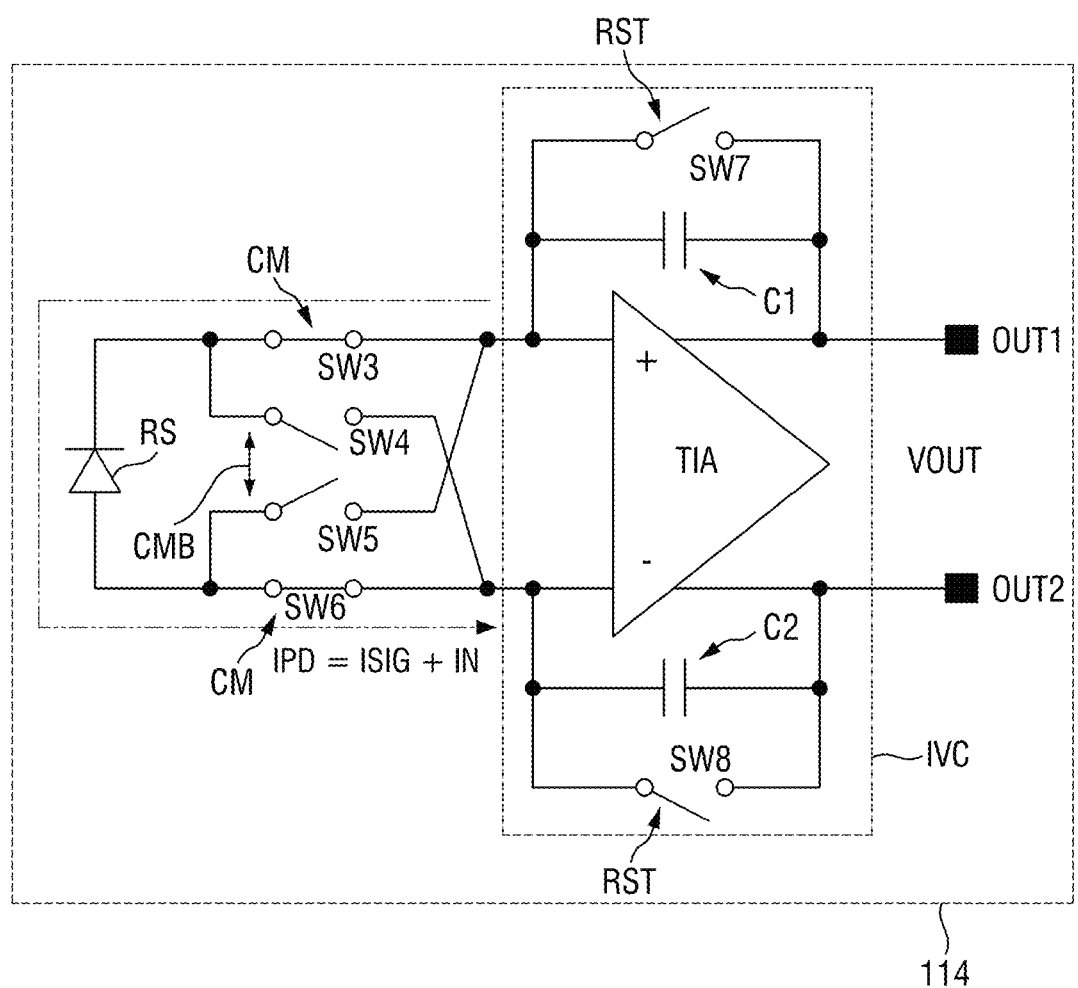
Figure 8:
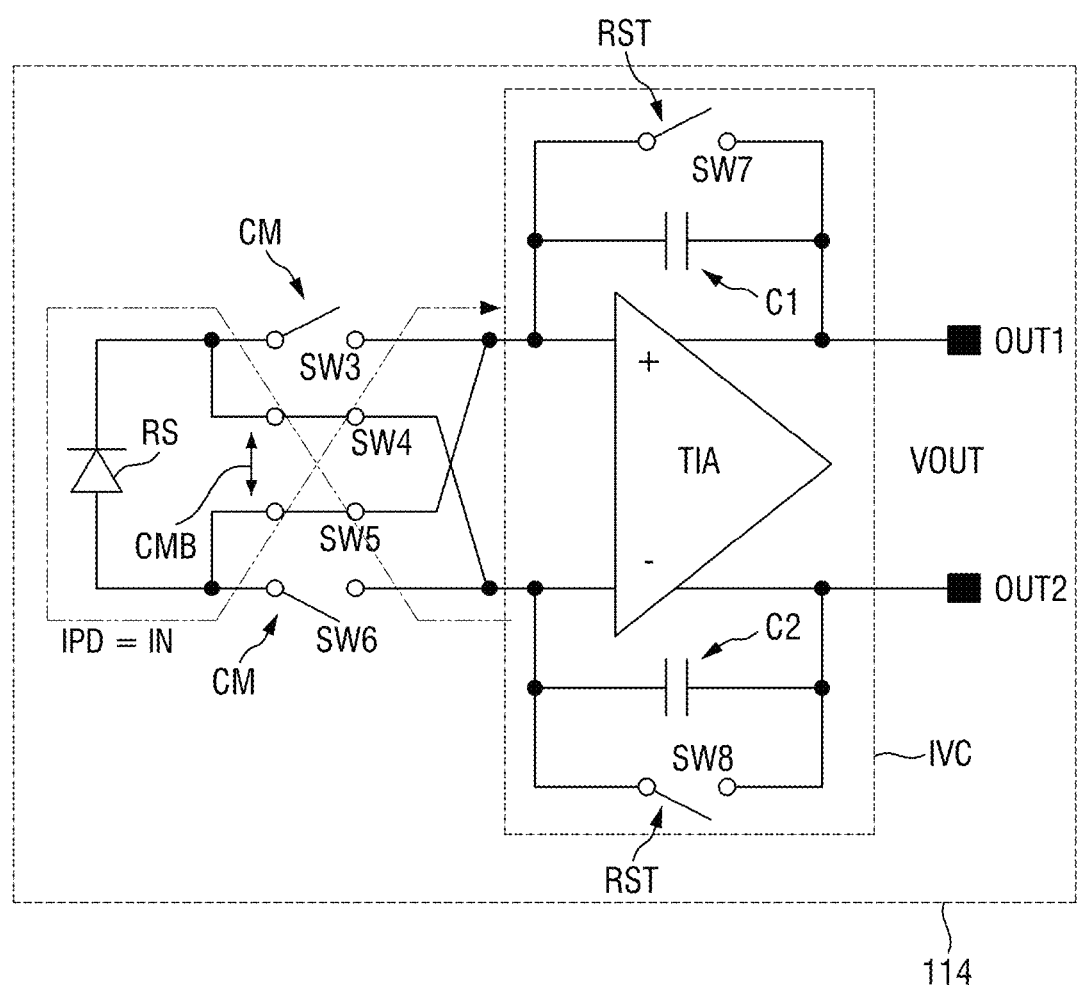

FIGS. 4 and 5 are timing diagrams describing an operation of a pulse wave sensor according to some example embodiments. FIGS. 6 to 8 are diagrams describing an operation of a pulse wave sensor according to some example embodiments.

First, referring to FIG. 4, the control signal CON transitions between the H-level and the L-level in a first period T1.

In addition, the control signal CM transitions between the H-level and the L-level in a second period T2 shorter than the first period T1.

Since the control signal CM, which is the modulation control signal, is repeated every second period T2, the light source 112 outputs a light pulse modulated with a frequency f1. Here, f1=1/T2 is established.

In some example embodiments, a section T3 in which the control signal CM maintains the H-level may be half of the second period T2. Since the light source 112 outputs the light L in a section where the control signal CM maintains the H-level, and does not output the light L in a section where the control signal CM maintains the L-level, a duty ratio of the light pulse outputted from the light source 112 may be substantially 0.5. However, example embodiments are not limited thereto, and the duty ratio of the light pulse may be variously modified as needed.

As described above, the light source 112 does not output the light L in the section where the control signal CON is at the L-level.

First, the reset control signal RST maintains the H-level during an initial time section t0. Accordingly, as shown in FIG. 6, the switches SW7 and SW8 are turned on and the storage elements C1 and C2 are initialized. Due to the initialization of the storage elements C1 and C2, the output voltage VOUT is also initialized (e.g., becomes zero).

Next, during a first time section t1, the reset control signal RST becomes the L-level and the switches SW7 and SW8 are turned off. In addition, the control signal CON and the control signal CM become the H-level, and the light L is outputted from the light source 112.

The light L outputted from the light source 112 is provided to the photoelectric conversion element RS in the form of the reflected light RL. Referring to FIG. 5, the reflected light RL received by the photoelectric conversion element RS has an intensity greater than that of the light L outputted from the light source 112 due to noise N. For example, the light source 112 may output the light L having only a signal component S, but the reflected light RL received by the photoelectric conversion element RS may include the signal component S and the noise N.

Referring to FIG. 7, since the control signal CM is at the H-level, the switches SW3 and SW6 are turned on, and the switches SW4 and SW5 are turned off. Accordingly, the cathode terminal of the photoelectric conversion element RS is connected to the first input terminal (+) of the current-to-voltage converter IVC, and the anode terminal of the photoelectric conversion element RS is connected to the second input terminal (−) of the current-to-voltage converter IVC.

Accordingly, a current IPD generated from the photoelectric conversion element RS flows in the illustrated direction. Since the reflected light RL received by the photoelectric conversion element RS includes the signal component S and the noise N, the current IPD includes a signal current ISIG and a noise current IN.

The current IPD generated from the photoelectric conversion element RS charges the storage elements C1 and C2 with electric charges. Accordingly, the amount of electric charges in the storage elements C1 and C2 increases corresponding to the signal current ISIG and the noise current IN. As the amount of electric charges in the storage elements C1 and C2 increases, an output voltage V1N including a signal component and a noise component is outputted to the output terminals OUT1 and OUT2.

In some example embodiments, the output voltage V1N may be calculated by, for example, the following equation.

$$V1N = ((ISIG+IN) \times t1)/\text{Capacitance of } C1, C2 \qquad \text{Eq. 1}$$

Referring to FIG. 4 again, the control signal CON maintains the H-level during a second time section t2 following the first time section t1, but the control signal CM becomes the L-level, and thus the light L is not outputted from the light source 112.

Referring to FIG. 5, since the light L is not outputted from the light source 112, the reflected light RL received by the photoelectric conversion element RS may include only the noise N.

Referring to FIG. 8, since the control signal CM is at the L-level, the switches SW3 and SW6 are turned off, and the switches SW4 and SW5 are turned on. Accordingly, the cathode terminal of the photoelectric conversion element RS is connected to the second input terminal (−) of the current-to-voltage converter IVC, and the anode terminal of the photoelectric conversion element RS is connected to the first input terminal (+) of the current-to-voltage converter IVC.

Accordingly, the current IPD generated from the photoelectric conversion element RS flows in the illustrated direction. Since the reflected light RL received by the photoelectric conversion element RS includes only noise N, the current IPD includes only the noise current IN.

The current IPD generated from the photoelectric conversion element RS discharges the electric charges from the storage elements C1 and C2. Accordingly, the amount of electric charges in the storage elements C1 and C2 decreases corresponding to the noise current IN. As the amount of electric charges in the storage elements C1 and C2 decreases, an output voltage V1 obtained by subtracting the noise component from the output voltage V1N is outputted to the output terminals OUT1 and OUT2.

At a time point when the second time section t2 has elapsed, the output voltage V1 may be calculated by, for example, the following equation.

$$V1 = (ISIG \times t1)/\text{Capacitance of } C1, C2 \qquad \text{Eq. 2}$$

At the time point when the second time section t2 has elapsed, since the amount of electric charges corresponding to the signal component has been stored in the storage elements C1 and C2, the amount of electric charges decreased in the storage elements C1 and C2 during the second time section t2 is less than the amount of electric charges increased in the storage elements C1 and C2 during the first time section t1.

Accordingly, the output voltage V1 is smaller than the output voltage V1N but larger than an initial voltage (e.g., zero).

Referring to FIG. 4 again, the control signal CM becomes the H-level again during a third time section t3 following the second time section t2, and the light L is outputted from the light source 112.

The light L outputted from the light source 112 is provided to the photoelectric conversion element RS in the form of the reflected light RL. In some example embodiments, the reflected light RL received by the photoelectric conversion element RS may include the signal component S and the noise N.

Referring to FIG. 7, since the control signal CM is at the H-level, the switches SW3 and SW6 are turned on, and the switches SW4 and SW5 are turned off. Accordingly, the cathode terminal of the photoelectric conversion element RS is connected to the first input terminal (+) of the current-to-voltage converter IVC, and the anode terminal of the photoelectric conversion element RS is connected to the second input terminal (−) of the current-to-voltage converter IVC.

Accordingly, the current IPD generated from the photoelectric conversion element RS flows in the illustrated direction. Since the reflected light RL received by the photoelectric conversion element RS includes the signal component S and the noise N, the current IPD includes the signal current ISIG and the noise current IN.

The current IPD generated from the photoelectric conversion element RS charges the storage elements C1 and C2 with electric charges. Accordingly, the amount of electric charges in the storage elements C1 and C2 increases corresponding to the signal current ISIG and the noise current IN from the amount of electric charges that has been stored in the storage elements C1 and C2 at the time point when the second time section t2 has elapsed. As the amount of electric charges in the storage elements C1 and C2 increases, an output voltage V2N including a signal component and a noise component is outputted to the output terminals OUT1 and OUT2.

Referring to FIG. 4 again, the control signal CON maintains the H-level during a fourth time section t4 following the third time section t3, but the control signal CM becomes the L-level, and thus the light L is not outputted from this light source 112. In some example embodiments, the reflected light RL received by the photoelectric conversion element RS may include only the noise N.

Referring to FIG. 8, since the control signal CM is at the L-level, the switches SW3 and SW6 are turned off, and the switches SW4 and SW5 are turned on. Accordingly, the cathode terminal of the photoelectric conversion element RS is connected to the second input terminal (−) of the current-to-voltage converter IVC, and the anode terminal of the photoelectric conversion element RS is connected to the first input terminal (+) of the current-to-voltage converter IVC.

Accordingly, the current IPD generated from the photoelectric conversion element RS flows in the illustrated direction. Since the reflected light RL received by the photoelectric conversion element RS includes only the noise N, the current IPD includes only the noise current IN.

The current IPD generated from the photoelectric conversion element RS discharges the electric charges from the storage elements C1 and C2. Accordingly, the amount of electric charges in the storage elements C1 and C2 decreases corresponding to the noise current IN from the amount of electric charges that has been stored in the storage elements C1 and C2 at a time point when the third time section t3 has elapsed. As the amount of electric charges in the storage elements C1 and C2 decreases, an output voltage V2 obtained by subtracting the noise component from the output voltage V2N is outputted to the output terminals OUT1 and OUT2.

At a time point when the fourth time section t4 has elapsed, since the amount of electric charges corresponding to the signal component has been stored in the storage elements C1 and C2, the amount of electric charges decreased in the storage elements C1 and C2 during the fourth time section t4 is less than the amount of electric charges increased in the storage elements C1 and C2 during the third time section t3.

Accordingly, the output voltage V2 is smaller than the output voltage V2N but larger than the output voltage V1.

If the above operation is repeated M times (M being a natural number), the current-to-voltage converter IVC may output an output voltage VM corresponding to the light L outputted from the light source 112 while the control signal CON maintains the H-level. Since the noise components received by the photoelectric conversion element RS have been sequentially removed step by step as described above, the output voltage VM corresponds only to the signal component of the light L outputted from the light source 112.

Hereinafter, the operation of the pulse wave sensor described above will be described in a frequency domain with reference to FIGS. 3 and 9 to 11.

Figure 9:
FIGS. 9 to 11 are diagrams describing an operation of a pulse wave sensor according to some example embodiments in a frequency domain.
Figure 10:
Figure 11:
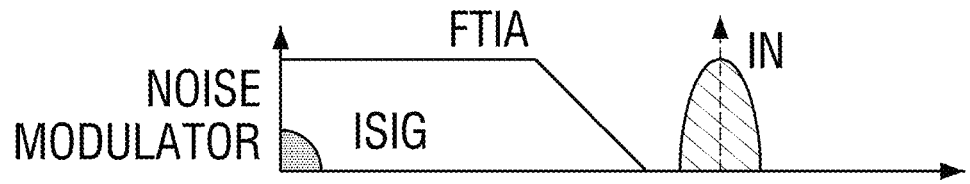

FIGS. 9 to 11 are diagrams describing an operation of a pulse wave sensor according to some example embodiments in a frequency domain.

Referring to FIGS. 3 and 9, as described above, the light source 112 of the pulse wave sensor according to the present example embodiments modulates the light L at a frequency of 1/T2 and outputs it. Accordingly, the light L outputted from the light source 112 has a frequency of 1/T2 in the frequency domain.

Next, referring to FIGS. 3 and 10, as described above, the reflected light RL received by the photoelectric conversion element RS has a signal component and a noise component. In addition, the photoelectric conversion element RS generates the current ISIG corresponding to the signal component and the current IN corresponding to the noise component.

The signal component of the reflected light RL has a frequency of 1/T2, but since the noise component has not been modulated at a specific frequency, the current ISIG and the current IN may be separated as shown in the frequency domain.

Next, referring to FIGS. 3 and 11, by the operation of the switches SW3, SW4, SW5, and SW6 described above, the current ISIG may be demodulated, and the current IN may be modulated. That is, the switches SW3, SW4, SW5, and SW6 may act as a modulator that demodulates the current ISIG and modulates the current IN. That is, in the present example embodiments, the modulator may be disposed in each of the light source 112 and the detector 114.

Depending on the operation of the switches SW3, SW4, SW5, and SW6, positions of the current ISIG and the current IN may be switched in the frequency domain. That is, the signal component does not have a frequency, and the noise component has a frequency of 1/T2.

The current-to-voltage converter IVG described above may act as a filter. For example, the current IN having a frequency of 1/T2 may be filtered by a bandwidth FTIA of the TIA of the current-to-voltage converter IVG.

Accordingly, the output voltage VOUT corresponding to the light L outputted from the light source 112 may be outputted to the output terminals OUT1 and OUT2 of the current-to-voltage converter IVG.

In the pulse wave sensor according to the present example embodiments, since the noise component is removed from the received light in such a manner, when the modulation operation of the light source 112 is properly adjusted, the noise may be effectively removed regardless of the signal sensitivity of the light L outputted from the light source 112. In addition, since a separate sampling circuit (e.g., a sample and hold circuit) is not required to remove the noise, the pulse wave sensor is advantageous in miniaturization.

Figure 12:
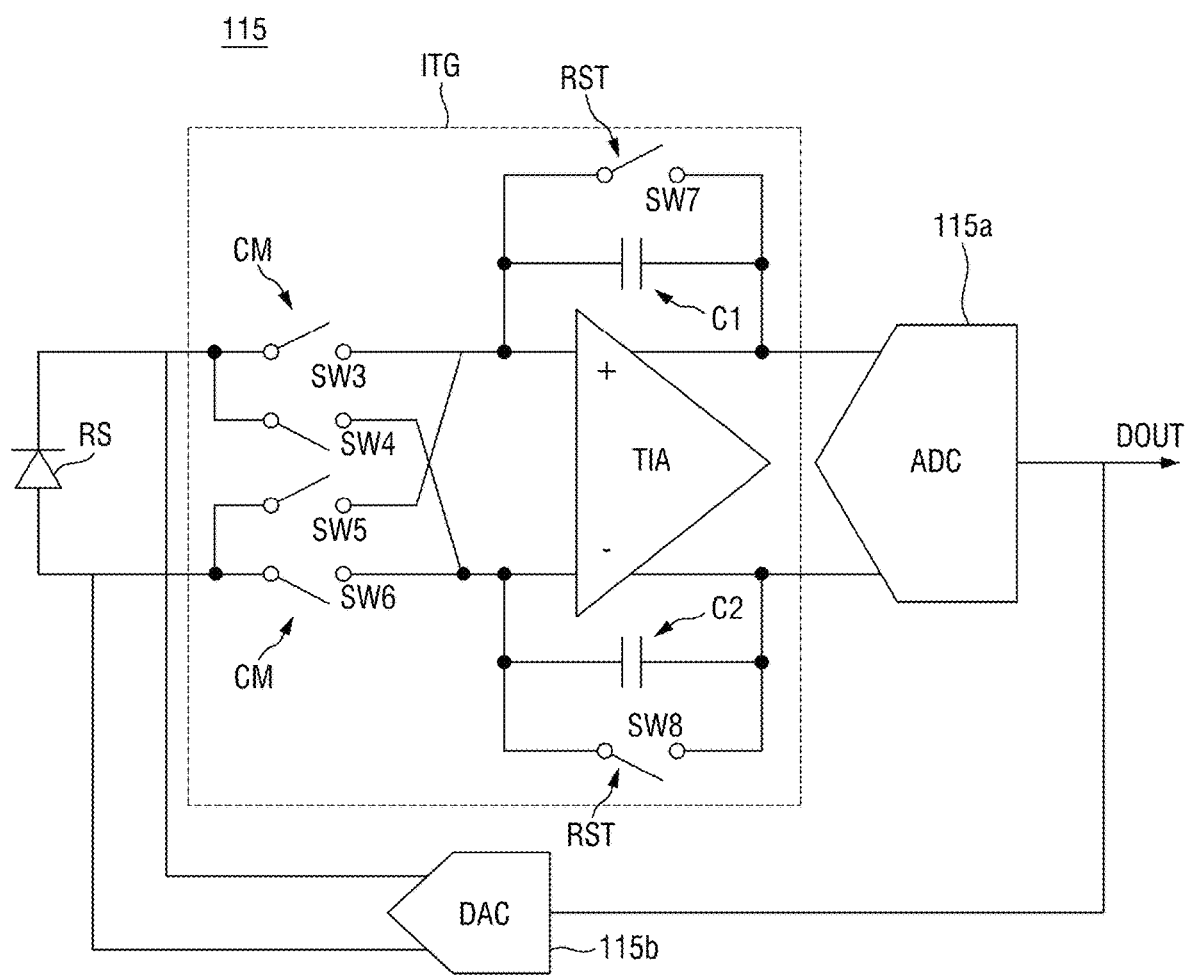
FIG. 12 is a circuit diagram of a pulse wave sensor according to some example embodiments.

FIG. 12 is a circuit diagram of a pulse wave sensor according to some example embodiments. Hereinafter, descriptions overlapping with the above-described example embodiments will be omitted, and differences will be mainly described.

Referring to FIG. 12, a pulse wave sensor 115 may include the switches SW3, SW4, SW5, and SW6, the TIA, an analog-to-digital converter 115a, and a digital-to-analog converter 115b, acting as a modulator.

In the present example embodiments, the switches SW3, SW4, SW5, and SW6, the TIA, the analog-to-digital converter 115a, and the digital-to-analog converter 115b may act as a sigma-delta modulator.

For example, when the switches SW3, SW4, SW5, and SW6 and the TIA acting as a modulator operate as an integrator to output a signal, the output signal may be converted into a digital signal DOUT according to the resolution of the analog-to-digital converter 115a, and the digital signal DOUT may be outputted. The output digital signal DOUT may be inputted to the digital-to-analog converter 115b and converted into an analog signal, and the analog signal may be provided again to the analog-to-digital converter 115a through the integrator.

According to some example embodiments, the illustrated pulse wave sensor 115 may further include a decimation filter, and when the pulse wave sensor 115 is configured in this way, it is possible to directly convert a pulse wave signal into a digital signal without an additional analog-to-digital conversion operation in a separate external read out circuit.

Figure 13:
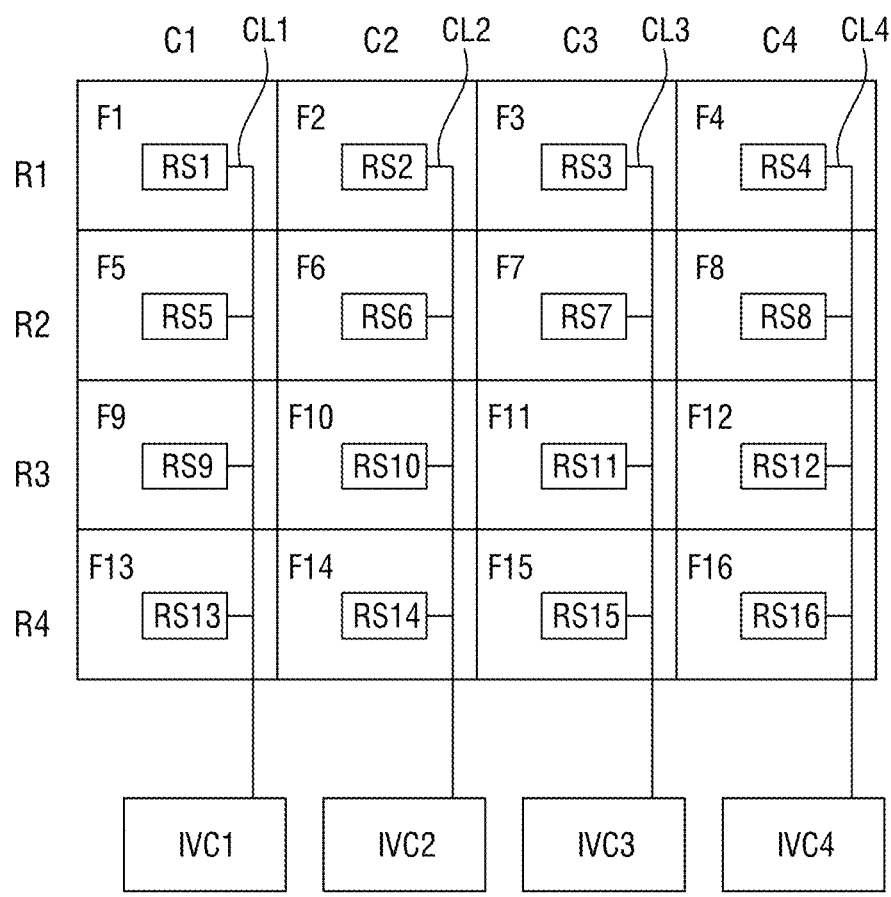
FIG. 13 is a conceptual diagram of a pulse wave sensor according to some example embodiments.

FIG. 13 is a conceptual diagram of a pulse wave sensor according to some example embodiments. Hereinafter, differences from the above-described example embodiments will be mainly described.

Referring to FIG. 13, a detector (e.g., the detector 114 of FIG. 1) of a pulse wave sensor 116 may include a plurality of photoelectric conversion elements RS1 to RS16 disposed in a plurality of rows R1 to R4 and a plurality of columns C1 to C4.

Although the drawing shows that the plurality of photoelectric conversion elements RS1 to RS16 are disposed in a 4×4 arrangement, example embodiments are not limited thereto. If necessary, the arrangement of the plurality of photoelectric conversion elements RS1 to RS16 may be variously modified.

The photoelectric conversion elements (e.g., RS1, RS2, RS3, and RS4) arranged in the same row (e.g., R1) may be connected to different columns, and the photoelectric conversion elements (e.g., RS1, RS5, RS9, and RS13) arranged in the same column (e.g., C1) may share the same column line.

Optical filters F1 to F16 may be disposed in the respective rows R1 to R4 and the respective columns C1 to C4. The optical filters F1 to F16 may filter light received by the pulse wave sensor 116 and provide it to the plurality of photoelectric conversion elements RS1 to RS16.

In some example embodiments, the optical filters F1 to F16 may have different optical characteristics. Accordingly, lights received by the photoelectric conversion elements RS1, RS4, RS13, and RS16 may all have different optical characteristics.

In addition, in some example embodiments, the optical filters F1 to F16 may be arranged to have the same optical characteristics for each row, or may be arranged to have the same optical characteristics for each column.

When the optical filters F1 to F16 are arranged to have the same optical characteristics for each row, the photoelectric conversion elements RS1 and RS4 may receive lights having the same optical characteristics, but the photoelectric conversion element RS13 may receive light having optical characteristics different from those of the photoelectric conversion elements RS1 and RS4.

Further, when the optical filters F1 to F16 are arranged to have the same optical characteristics for each column, the photoelectric conversion elements RS1 and RS13 may receive lights having the same optical characteristics, but the photoelectric conversion element RS2 may receive light having optical characteristics different from those of the photoelectric conversion elements RS1 and RS13.

Each of column lines CL1, CL2, CL3, and CL4 may be shared between the photoelectric conversion elements RS1 to RS16 disposed in the same column. That is, the column line CL1 may connect the photoelectric conversion elements RS1, RS5, RS9, and RS13 to a current-to-voltage converter IVC1, and the column line CL2 may connect the photoelectric conversion elements RS2, RS6, RS10, and RS14 to a current-to-voltage converter IVC2, the column line CL3 may connect the photoelectric conversion elements RS3, RS7, RS11, and RS15 to a current-to-voltage converter IVC3, and the column line CL4 may connect the photoelectric conversion elements RS4, RS8, RS12, and RS16 to a current-to-voltage converter IVC4.

Figure 14:
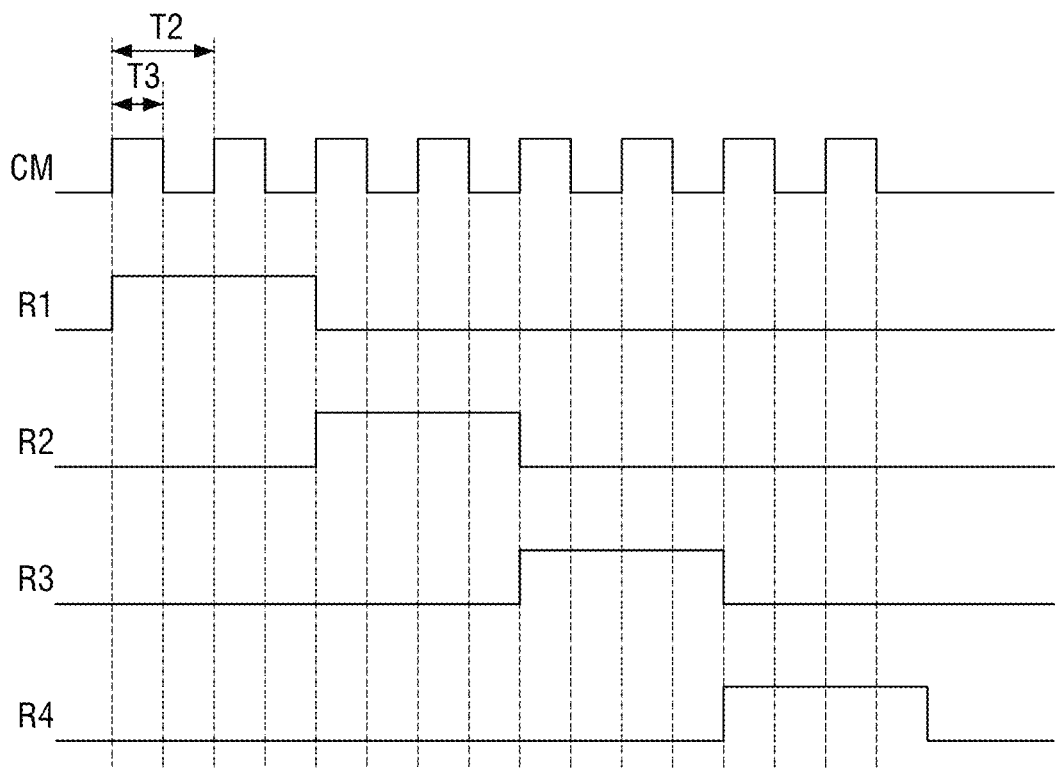
FIG. 14 is a timing diagram describing an operation of the pulse wave sensor of FIG. 13.

FIG. 14 is a timing diagram describing an operation of the pulse wave sensor of FIG. 13.

Referring to FIG. 14, the rows R1 to R4 may be sequentially selected while the control signal CM transitions between the H-level and the L-level.

For example, the row R1 may be selected and then unselected while the control signal CM transitions between the H-level and the L-level twice (e.g., while the light pulse outputted from the light source is received twice). The row R2 may be selected after the row R1 is unselected, and may be selected and then unselected while the control signal CM transitions between the H-level and the L-level twice. The rows R3 and R4 may also be selected sequentially in the same manner.

Although the drawing shows an example in which each of the rows R1 to R4 is selected in a cycle of receiving the light pulse outputted from the light source twice, example embodiments are not limited thereto. If necessary, the cycle may be variously modified and implemented.

In addition, in some example embodiments, the rows R1 and R3 may be simultaneously selected, and the rows R2 and R4 may be simultaneously selected.

In the case of sensing a pulse wave signal based on lights having different optical characteristics as described above, a processor (e.g., the processor 120 of FIG. 1) may perform more various processing.

Figure 15:
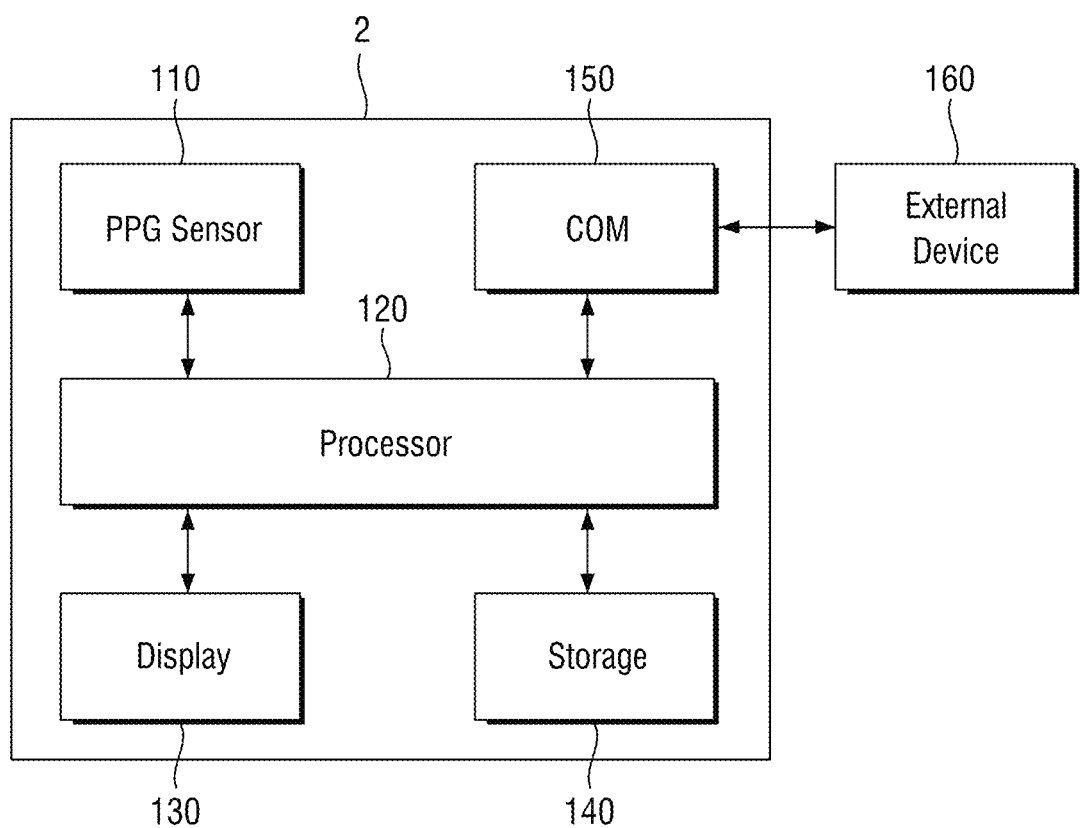
FIG. 15 is a block diagram of an electronic device according to some example embodiments.

FIG. 15 is a block diagram of an electronic device according to some example embodiments.

Referring to FIG. 15, an electronic device 2 may include a pulse wave sensor 110, a processor 120, an output unit 130, a storage unit 140, and/or a communication unit 150.

As the pulse wave sensor 110, the pulse wave sensor 110 according to various example embodiments described above may be employed.

The processor 120 may perform the same or substantially the same operation as the processor 120 previously described with reference to FIG. 1.

The output unit 130 may output a processing result of the processor 120 to a user. For example, the output unit 130 may visually output a heart rate, a pulse rate, a blood pressure, a blood glucose estimation value, and the like through a display module. Alternatively, the output unit 130 may output the same in a non-visual manner such as voice, vibration, or tactile sensation through a speaker module, a haptic module, or the like.

The output unit 130 may divide a display area into two or more parts according to a setting and may output biometric information extracted by the processor 120 for each part.

The storage unit 140 may store the processing result of the processor 120 therein. In addition, the storage unit 140 may store reference information required for signal processing of the processor 120. For example, the reference information may include user characteristic information such as age, gender, and health condition of the user.

The storage unit 140 may include a storage medium such as a flash memory type memory, a hard disk type memory, a multimedia card micro type memory, and a card type memory (e.g., a secure digital (SD) or extreme digital (XD) memory), a random access memory (RAM), a static random access memory (SRAM), a read-only memory (ROM), an electrically erasable programmable read-only memory (EEPROM), a programmable read-only memory (PROM), a magnetic memory, a magnetic disk, or an optical disk, but example embodiments are not limited thereto.

The communication unit 150 may communicate with an external device 160 to transmit and receive various types of data using wired/wireless communication technology under the control of the processor 120. For example, the communication unit 150 may transmit the biometric information to the external device 160. In addition, the communication unit 150 may receive various signals required to estimate the biometric information from the external device 160.

The external device 160 may include an information processing device such as a wearable device, a smart phone, a tablet PC, a desktop PC, or a notebook PC.

According to some example embodiments, the communication technology may include Bluetooth communication, Bluetooth Low Energy (BLE) communication, near field communication (NFC), WLAN communication, Zigbee communication, infrared data association (IrDA) communication, Wi-Fi Direct (WFD) communication, ultra-wideband (UWB) communication, Ant+ communication, Wi-Fi communication, radio frequency identification (RFID) communication, 3G communication, 4G communication and 5G communication, and the like, but example embodiments are limited thereto.

Any of the elements disclosed above may include or be implemented in processing circuitry such as hardware including logic circuits; a hardware/software combination such as a processor executing software; or a combination thereof. For example, the processing circuitry more specifically may include, but is not limited to, a central processing unit (CPU), an arithmetic logic unit (ALU), a digital signal processor, a microcomputer, a field programmable gate array (FPGA), a System-on-Chip (SoC), a programmable logic unit, a microprocessor, application-specific integrated circuit (ASIC), etc.

In concluding the detailed description, those skilled in the art will appreciate that many variations and modifications may be made to the preferred example embodiments without substantially departing from the principles of the present inventive concepts. Therefore, the disclosed preferred example embodiments of the inventive concepts are used in a generic and descriptive sense only and not for purposes of limitation.

What is claimed is:

1. A photoplethysmography sensor comprising:
   a photoelectric conversion element including a cathode terminal and an anode terminal, the photoelectric conversion element configured to receive light reflected from a blood vessel and generate a current corresponding to the received light;
   a current-to-voltage converter including a first input terminal and a second input terminal, the current-to-voltage converter configured to receive the generated current as a received current through the first input terminal and the second input terminal, and the current-to-voltage converter configured to generate an output voltage corresponding to the received current; and
   a switch configured to connect the photoelectric conversion element to the current-to-voltage converter according to a control signal,
   wherein in response to the control signal of a first level, the switch directly connects the cathode terminal of the photoelectric conversion element to the first input terminal of the current-to-voltage converter, and directly connects the anode terminal of the photoelectric conversion element to the second input terminal of the current-to-voltage converter, and
   wherein in response to the control signal of a second level different from the first level, the switch directly connects the cathode terminal of the photoelectric conversion element to the second input terminal of the current-to-voltage converter, and directly connects the anode terminal of the photoelectric conversion element to the first input terminal of the current-to-voltage converter.

2. The photoplethysmography sensor of claim 1, wherein the current-to-voltage converter includes:
   a transimpedance amplifier (TIA) including the first input terminal and the second input terminal; and
   a storage unit connected to at least one of the first input terminal of the TIA or the second input terminal of the TIA and an output terminal of the TIA, the storage unit configured to store the output voltage.

3. The photoplethysmography sensor of claim 2, wherein the storage unit includes a first storage element and a second storage element,
   the output terminal of the TIA includes a first output terminal and a second output terminal,
   the first storage element is connected to the first input terminal of the TIA and the first output terminal of the TIA, and
   the second storage element is connected to the second input terminal of the TIA and the second output terminal of the TIA.

4. The photoplethysmography sensor of claim 2, wherein while the control signal is at the first level, an amount of electric charge in the storage unit increases corresponding to the current generated from the photoelectric conversion element, and
   while the control signal is at the second level, the amount of electric charge in the storage unit decreases corresponding to the current generated from the photoelectric conversion element.

5. The photoplethysmography sensor of claim 4, further comprising a light source configured to output the light in response to the control signal of the first level, and configured not to output the light in response to the control signal of the second level.

6. The photoplethysmography sensor of claim 5, wherein the control signal includes a first control signal and a second control signal,
   the switch connects the photoelectric conversion element to the current-to-voltage converter according to the second control signal, and
   the light source outputs the light in response to the first control signal of the first level and the second control signal of the first level.

7. The photoplethysmography sensor of claim 1, wherein the switch includes:
   a first switch configured to connect the cathode terminal of the photoelectric conversion element to the first input terminal of the current-to-voltage converter in response to the control signal of the first level;

a second switch configured to connect the cathode terminal of the photoelectric conversion element to the second input terminal of the current-to-voltage converter in response to the control signal of the second level;

a third switch configured to connect the anode terminal of the photoelectric conversion element to the first input terminal of the current-to-voltage converter in response to the control signal of the second level; and a fourth switch configured to connect the anode terminal of the photoelectric conversion element to the second input terminal of the current-to-voltage converter in response to the control signal of the first level.

8. The photoplethysmography sensor of claim 7, further comprising a light source configured to output the light in response to the control signal of the first level, and configured not to output the light in response to the control signal of the second level, wherein the control signal includes:

a first control signal having a first period; and a second control signal having a second period shorter than the first period, and wherein the first to fourth switches are configured to connect the photoelectric conversion element to the current-to-voltage converter according to the second control signal, and the light source outputs the light in response to the first control signal of the first level and the second control signal of the first level.

9. A photoplethysmography sensor comprising:

a photoelectric conversion element including a cathode terminal and an anode terminal, the photoelectric conversion element configured to receive light reflected from a blood vessel and generate a current corresponding to the received light;

a current-to-voltage converter having a first input terminal and a second input terminal, the current-to-voltage converter configured to receive the generated current as a received current through the first input terminal and the second input terminal, and the current-to-voltage converter configured to generate an output voltage corresponding to the received current, the current-to-voltage converter comprising a transimpedance amplifier (TIA) including the first input terminal and the second input terminal, and a storage unit connected to at least one of the first input terminal of the TIA or the second input terminal of the TIA, and the storage unit connected to an output terminal of the TIA, the storage unit configured to store the output voltage; and a switch configured to directly connect the cathode terminal to the first input terminal and the anode terminal to the second input terminal to connect the generated current to directly flow into the current-to-voltage converter in a first direction to increase an amount of electric charge in the storage unit responsive to a control signal at a first level, and to directly connect the cathode terminal to the second input terminal and the anode terminal to the first input terminal to connect the generated current to directly flow into the current-to-voltage converter in a second direction different than the first direction to decrease the amount of electric charge in the storage unit responsive to the control signal at a second level different than the first level.

10. The photoplethysmography sensor of claim 9, wherein the storage unit includes a first storage element and a second storage element, the output terminal of the TIA includes a first output terminal and a second output terminal, the first storage element is connected to the first input terminal of the TIA and the first output terminal of the TIA, and the second storage element is connected to the second input terminal of the TIA and the second output terminal of the TIA.

11. The photoplethysmography sensor of claim 10, further comprising a light source configured to output the light in response to the control signal of the first level, and configured not to output the light in response to the control signal of the second level.

12. The photoplethysmography sensor of claim 11, wherein the control signal includes a first control signal and a second control signal, the switch connects the photoelectric conversion element to the current-to-voltage converter according to the second control signal, and the light source outputs the light in response to the first control signal of the first level and the second control signal of the first level.

13. The photoplethysmography sensor of claim 9, wherein the switch comprises:

a first switch configured to directly connect the cathode terminal of the photoelectric conversion element to the first input terminal of the current-to-voltage converter in response to the control signal of the first level;

a second switch configured to directly connect the cathode terminal of the photoelectric conversion element to the second input terminal of the current-to-voltage converter in response to the control signal of the second level;

a third switch configured to directly connect the anode terminal of the photoelectric conversion element to the first input terminal of the current-to-voltage converter in response to the control signal of the second level; and a fourth switch configured to directly connect the anode terminal of the photoelectric conversion element to the second input terminal of the current-to-voltage converter in response to the control signal of the first level.

14. The photoplethysmography sensor of claim 13, further comprising a light source configured to output the light in response to the control signal of the first level, and configured not to output the light in response to the control signal of the second level, wherein the control signal includes a first control signal having a first period, and a second control signal having a second period shorter than the first period, and wherein the first to fourth switches are configured to connect the photoelectric conversion element to the current-to-voltage converter according to the second control signal, and the light source outputs the light in response to the first control signal of the first level and the second control signal of the first level.

15. The photoplethysmography sensor of claim 9, wherein the amount of electric charges in the storage unit increases corresponding to electric charges generated by the photoelectric conversion element during a first time section, and decreases corresponding to electric charges generated by the photoelectric conversion element during a second time section following the first time section.

16. The photoplethysmography sensor of claim 15, wherein an amount of electric charges increased in the storage unit during the first time section is greater than an amount of electric charges decreased in the storage unit during the second time section.

17. A method of operating a photoplethysmography sensor, the photoplethysmography sensor including
- a photoelectric conversion element including a cathode terminal and an anode terminal, the photoelectric conversion element configured to generate electric charge corresponding to received light reflected from a blood vessel,
- a current-to-voltage converter including a first input terminal and a second input terminal, the current-to-voltage converter configured to output an output voltage to an output node based on the generated electric charge, and
- a switch configured to connect the photoelectric conversion element to the current-to-voltage converter, the method comprising:
- outputting, to the output node, a first output voltage corresponding to the received light during a first time section; and
- outputting a second output voltage smaller than the first output voltage to the output node, the second output voltage corresponding to the received light during a second time section following the first time section,
- wherein during the first time section the switch directly connects the cathode terminal of the photoelectric conversion element to the first input terminal of the current-to-voltage converter, and directly connects the anode terminal of the photoelectric conversion element to the second input terminal of the current-to-voltage converter, and
- during the second time section the switch directly connects the cathode terminal of the photoelectric conversion element to the second input terminal of the current-to-voltage converter, and directly connects the anode terminal of the photoelectric conversion element to the first input terminal of the current-to-voltage converter.

18. The method of claim 17, further comprising:
- outputting a third output voltage greater than the second output voltage to the output node, the third output voltage corresponding to the received light during a third time section following the second time section; and
- outputting a fourth output voltage smaller than the third output voltage to the output node, the fourth output voltage corresponding to the received light during a fourth time section following the third time section.

19. The method of claim 18, wherein the photoelectric conversion element includes:
- a first photoelectric conversion element in a first row of an array of photoelectric conversion elements and associated with generation of the first and second output voltages; and
- a second photoelectric conversion element in a second row of the array of photoelectric conversion elements and associated with generation of the third and fourth output voltages.

* * * * *